United States Patent [19]

Röhricht et al.

[11] 4,342,755
[45] Aug. 3, 1982

[54] TRANQUILLO-SEDATIVE BENZODIAZEPINE DERIVATIVES

[75] Inventors: Julia Röhricht; Lajos Kisfaludy; László Ürögdi; Éva Pálosi; Szabolcs Szeberényi; László Szporny, all of Budapest, Hungary

[73] Assignee: Richter Gedeon Vegyeszeti Gyar RT, Budapest, Hungary

[21] Appl. No.: 185,512

[22] Filed: Sep. 9, 1980

Related U.S. Application Data

[63] Continuation-in-part of Ser. No. 795,894, May 11, 1977, abandoned, which is a continuation-in-part of Ser. No. 580,307, May 23, 1975, Pat. No. 4,045,433.

[30] Foreign Application Priority Data

May 29, 1974 [HU] Hungary .................... RI-538

[51] Int. Cl.³ .................... A61K 31/55; C07D 243/24
[52] U.S. Cl. .................... 424/244; 260/239.3 D
[58] Field of Search ................. 260/239.3 D; 424/244

[56] References Cited

FOREIGN PATENT DOCUMENTS 48-25199 7/1973 Japan ........................ 260/239.3 D

OTHER PUBLICATIONS

March "Advanced Organic Chemistry" (Mc-Graw Hill), (1968) p. 335.

Primary Examiner—Robert T. Bond
Attorney, Agent, or Firm—Karl F. Ross

[57] ABSTRACT

A tranquillo-sedative substituted 1,3,4,5-tetrahydro-2H-1,4-benzodiazepine-2-one of the formula (I),

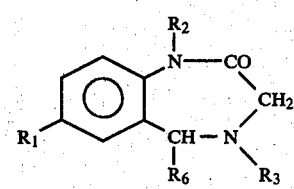

wherein
  $R_1$ is halogen or nitro,
  $R_2$ is hydrogen or $C_1$ to $C_6$ alkyl,
  $R_3$ is —$CONH_2$, and
  $R_6$ is phenyl or halophenyl.

4 Claims, No Drawings

TRANQUILLO-SEDATIVE BENZODIAZEPINE DERIVATIVES

CROSS REFERENCE TO RELATED APPLICATION

This application is a continuation-in-part of Ser. No. 795,894 filed May 11, 1977, now abandoned, which is a continuation-in-part of Ser. No. 580,307 filed May 23, 1975, now U.S. Pat. No. 4,045,433.

This invention relates to new benzodiazepine derivatives.

More particularly, the invention relates to racemic $N^4$-acyl-1,3,4,5-tetrahydro-2H-1,4-benzodiazepine-2-one derivatives of the formula (I)

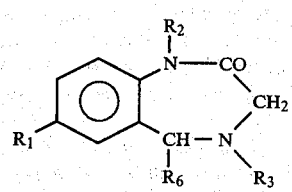

wherein
$R_1$ is hydrogen or nitro,
$R_2$ is hydrogen or $C_1$ to $C_6$ alkyl,
$R_3$ is —$CONH_2$, and
$R_6$ is phenyl or halophenyl.

Furthermore the invention relates to the optically active $N^4$-acyl-1,3,4,5-tetrahydro-2H-1,4-benzodiazepine-2-one derivatives of the formula (I).

All the above compounds are novel.

The compounds according to the invention possess tranquilizing (anxiolytic) and anticonvulsive activities.

Owing to their excellent tranquilizing (anxiolytic) and anticonvulsive effects, some of the hitherto known 1,4-benzodiazepine derivatives have attained great practical use.

Based on the examination of the known compounds, some conclusions can be drawn with respect to the relationship of the chemical structures and pharmaceutical effects. It has been stated, inter alia, that the presence of a double bond between positions 4 and 5 is absolutely necessary to obtain a compound with high activity, since the tetrahydro derivatives obtained by saturating this double bond showed far lower activities in pharmacological tests than the respective unsaturated compounds. This low activity decreases further when a substituent is attached to position $N^4$ (L. H. Sternbach et al.: Drugs Affecting the Central Nervous System, A. Burger, ed., 1968, vol. 2, page 237). These facts explain why the number of tetrahydro-benzodiazepine derivatives prepared to date is far lower than that of the dihydro compounds.

Intermediate compounds according to the following formula are also contemplated as part of the invention:

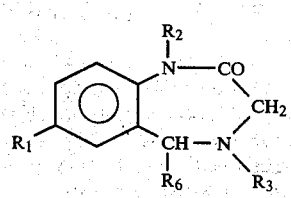

wherein
$R_1$ is hydrogen or nitro;
$R_2$ is hydrogen or $C_1$ to $C_6$ alkyl;
$R_3$ is chlorocarbonyl; and
$R_6$ is phenyl or halophenyl.

Up to now the following methods were utilized for the preparation of 4-substituted-tetrahydro-1,4-benzodiazepine derivatives;

1-Monosubstituted and 1,4-disubstituted-tetrahydrobenzodiazepine derivatives were prepared by the direct alkylation of 1,4-tetrahydro-benzodiazepine (J. Med. Chem. 7, 386; 1964; French Pat. No. 1,339,762).

According to U.S. Pat. No. 3,501,474 and Dutch patent application No. 69-17,320 the $N^4$-substituted-tetrahydro-1,4-benzodiazepine-2-one derivatives were prepared from the appropriate isoquinoline compounds by ring expansion.

Japanese Pat. No. 48-25,199 describes the preparation of tetrahydro-1,4-benzodiazepine-2-one derivatives having a substituted carbamoyl group in position 4.

Contrary to previous experience we have found that the 4-substituted-tetrahydro-1,4-benzodiazepine derivatives of the formula (I), wherein $R_1$, $R_2$, $R_3$ and $R_4$ each have the meanings given above, possess strong pharmaceutical effects.

In these compounds $R_1$ can be fluorine, chlorine, bromine or iodine, preferably chlorine, as the halogen atom.

As the alkyl group, $R_2$ is a straight-chain or branched alkyl group, preferably a lower alkyl group with 1 to 6 carbon atoms. Such groups can be methyl, ethyl, n-propyl, isopropyl, n-butyl, iso-butyl, t-butyl, amyl, isoamyl and hexyl. A preferred alkyl group is methyl.

As mentioned above, a halogen atom is optionally attached to the $R_6$ phenyl group. This halogen substituent can be fluorine, chlorine, bromine or iodine, and preferably is in the ortho position of the phenyl group.

The alkyl groups mentioned in the specification can be methyl, ethyl, n-propyl, isopropyl, n-butyl, isobutyl, amyl, isoamyl or isomeric hexyl groups.

The most preferred representatives of the above compounds are those wherein $R_1$ is chlorine or nitro, $R_2$ is methyl, $R_3$ $CONH_2$ and $R_6$ is phenyl or halophenyl.

Of the compounds of the formula (I) 1-methyl-4-carbamoyl-5-phenyl-7-chloro-1,3,4,5-tetrahydro-2H-1,4-benzodiazepine-2-one has proved to be the most effective.

The compounds of the formula (I) can be prepared as follows:

(a) A 1,3,4,5-tetrahydro-2H-1,4-benzodiazepine-2-one derivative of the formula (II),

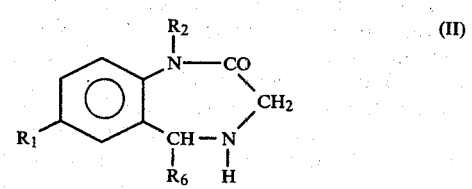

wherein $R_1$, $R_2$ and $R_6$ each have the meanings defined above, is reacted, optionally in the presence of an acid binding agent, with phosgene, then with ammonia, or (b) A 1,3,4,5-tetrahydro-2H-1,4-benzodiazepine-2-one derivative of the formula (II) or a salt thereof is reacted with an alkali metal cyanate.

All compounds prepared by the above process are novel.

The starting substances of the formula (II) can be prepared as described in Hungarian Pat. No. 155,251.

The alkali metal atom is preferably potassium.

In process variant (a), the reaction is performed preferably in the presence of an acid binding agent in order to ensure a quick and complete reaction. As the acid binding agent, e.g. an inorganic base, such as a metal oxide, preferably an alkaline-earth metal oxide (e.g. magnesium oxide), an alkali metal hydrocarbonate, an alkali metal carbonate, such as potassium carbonate, or a tertiary organic base, such as pyridine or a tertiary amine (e.g. triethylamine), etc. can be used. The amount of the acid binding agent may vary within wide limits, but the acid binding agent is used preferably at least in an amount necessary to bind all of the acid formed in this reaction. The reaction is carried out in an organic liquid inert towards the chemical procedure; depending on the solubility characteristics of the starting substances, this organic liquid may serve either as a solvent or as a suspending agent. Of these organic liquids, e.g. the halogenated hydrocarbons (such as chloroform, carbon tetrachloride, dichlormethane, 1,2-dichlorethane, trichlorethylene, etc.), the aromatic hydrocarbons (such as benzene or toluene), acetone, dioxane, tetrahydrofuran, dimethyl formamide and dimethyl sulfoxide are mentioned specifically. The reaction temperature may vary within wide limits, e.g. between 0° C. and 180° C., but it is preferred to conduct the reaction at about room temperature. The reaction time varies depending on the starting substances, the solvent and the reaction temperature, and is generally between 1 and 12 hours, preferably between 3 and 6 hours.

According to the process variant (a) a solution or a suspension of a tetrahydro-1,4-benzodiazepine-2-one derivative of the formula (II) is treated at room temperature, in the presence of an inorganic binding agent (such as magnesium oxide or sodium bicarbonate) or a tertiary organic base (such as triethylamine), with phosgene. The process of the reaction is monitored by thin-layer chromatography. When the reaction terminates, the mixture is processed.

The reaction mixture can be processed by various methods depending upon the nature of the starting substances, the end-product and the solvent. One may proceed, e.g. by removing the optionally separated salts by filtration and evaporating the filtrate to dryness.

The process variant (a) yields a compound of the formula (I) wherein $R_3$ is a halocarbonyl, preferably a chlorocarbonyl group. These compounds can be reacted with ammonia.

This reaction is conducted preferably in the presence of an acid-binding agent. As acid-binding agent an excess of the amine reactant can be employed, but an inorganic base, such as magnesium oxide or sodium bicarbonate, may be used as well.

The reaction is performed preferably in the presence of an inert solvent, such as methanol, ethanol, chloroform, carbon tetrachloride, benzene, aqueous methanol, etc.

In process variant (b), the compounds of the formula (II) are used preferably in the form of their acid-addition salts. The most appropriate acid-addition salts are the hydrohalides, such as the hydrochlorides or hydrobromides, but salts formed with other mineral or organic acids, such as phosphoric acid, acetic acid, propionic acid, benzoic acid, etc. may be used as well. According to a preferred method one can proceed by dissolving a compound of the formula (II) in an inert organic solvent, introducing dry gaseous hydrogen chloride into the solution, filtering off the separated hydrochloride, suspending the same without drying in the solvent used for the next reaction step, and then introducing an alkali metal cyanate. Any solvent inert to the reaction, such as the solvents mentioned in connection with process variant (a), can be used, but acetic acid has proven to be particularly preferable. The reaction temperature may vary within wide limits and has no decisive significance, but it is preferred to conduct the reaction at about room temperature. Depending on the starting substance, the solvent and the reaction temperature, the reaction time may range from about 20 minutes to about 10 hours.

The above procedure is performed preferably by suspending a mineral acid salt of a compound of the formula (II), preferably hydrochloride, in an organic liquid, and reacting it at room temperature with potassium cyanate.

Any of the compounds having the formula (I), wherein $R_2$ is hydrogen, can be alkylated, if desired, to obtain the respective $R_2$=alkyl derivatives. In this reaction conventional alkylating agents, such as alkyl halides (preferably alkyl iodides) or dialkyl sulfates can be used.

One can proceed by converting first a compound of the formula (I) into its alkali metal derivative, and reacting the thus-obtained alkali metal compound with an appropriate alkylating agent. The alkali metal compound can be prepared by reacting the appropriate compound of the formula (I), wherein $R_2$ is hydrogen with an alkali metal, alkali hydroxide or alkali amide, particularly with sodium or with a sodium compound, at 0° to 150° C. in an inert solvent, such as dioxane, dimethyl formamide, benzene or toluene.

When processing the reaction mixture the product is generally obtained in crystalline form. If, however, an oily substance is obtained, this can be crystallized generally very easily using conventional solvents, e.g. aliphatic or cyclic ethers, such as diethyl ether, dioxane, tetrahydrofuran, etc.

If necessary, the compounds of the formula (I) can be subjected to additional purification steps, such as recrystallization. As recrystallization solvent we can use an aliphatic alcohol, such as methanol or ethanol, an aromatic hydrocarbon, such as benzene, a ketone, such as acetone, an aliphatic ester, particularly an alkanecarboxylate such as ethyl acetate, an aliphatic hydrocarbon, particularly a $C_{5-10}$ saturated aliphatic hydrocarbon such as n-hexane, an ether, particularly a dialkyl ether such as diethyl ether, a saturated cyclic ether, such as tetrahydrofuran, acetonitrile, as well as the mixtures thereof (e.g. a mixture of tetrahydrofuran and hexane or a mixture of ethyl acetate and ether).

The process according to the invention provides the compounds of the formula (I) with high yields and in easily identifiable state. The elemental analysis data of the obtained substances are in good agreement with the calculated values.

Depending on whether a racemic or an optically active starting substance of the formula (II) is used, the end-products of the formula (I) can be obtained in racemic or optically active forms.

The 4-substituted-1,3,4,5-tetrahydro-2H-1,4-benzodiazepine-2-one derivatives according to the invention possess excellent tranquilizing (anxiolytic) and anticonvulsive activities. The most valuable representative of these compounds is 1-methyl-4-carbamoyl-5-phenyl-7-chloro-1,3,4,5-tetrahydro-2H-1,4-benzodiazepine-2-one.

The pharmacological tests were carried out according to the following methods:

The tests were performed on CFLP mice of both sexes, weighing 18 to 22 g. In the screen tests the chemicals were administered intraperitoneally, one hour prior to starting the tests. 1-Methyl-4-carbamoyl-5-phenyl-7-chloro-1,3,4,5-tetrahydro-2H-1,4-benzodiazepine-2-one, the most active representative of the compounds according to the invention, as well as the reference substances (Diazepam and Chlorodiazepoxide) were administered orally one hour prior to starting the examinations.

Examination of anti-convulsant activity (1) The first series of examinations was carried out according to the method of Everett and Richards [Everett, G. M., Richards, R. K.: J. Pharm. Exp. Ther. 81, 402 (1944)]. 125 mg/kg of metrazole were administered subcutaneously to the test animals. 1 hours after the administration the animals protected from tonic extensor spasm and the surviving animals were counted. The $ED_{50}$ values were determined from these data by probit analysis.

(2) Maximum electroshock stimulus (100 Hz, 30 V, 0.2 sec.) was applied according to the method of Swinyard et al. [Swinyard, E. A., Brown, W. C., Goodman, L. S.: J. Pharm. 106, 319 (1952)]. The animals showing no tonic extension on the hind limb upon stimulus were considered as protected.

Antagonism of strychnine spasm

Tonic extensor spasm was produced by administering an intraperitoneal dosage of 2 mg/kg of strychnine to the animals [Kerley, T. L., Richards, A. G. Begley, R. W., Abren, B. E. and Weaver, L. C.: J Pharm. Exp. Ther. 132, 360 (1961)]. The animals showing no spasm were considered as protected.

Examination of muscle incoordination and atexia (a) Rotarod test: the test was carried out according to the method of Kinnard and Carr [Brit. J. Pharm. Exp. Ther. 121, 354 (1957)]. The control animals were able to stay for 120 secods on a rod rotated at 12 revolutions per min. The $ED_{50}$ values were calculated from the percentage of the animals falling down within 120 seconds.

(b) Traction test: the test was carried out according to the method of Theobald et al [Arch. int. Pharmacodyn. 148, 560 (1964)]. The two anterior limbs of the test animals were placed onto a horizontal rod so as to let the animals clutch the rod. The control animals pulled their hind limbs onto the rod within 5 seconds. The $ED_{50}$ values were calculated from the percentage of the animals showing negative response.

Examination of narcosis potentiating effect

As is known, the liver cannot metabolize sodium barbiturate [Ebert, A. G., Yim, G. K. W., Miya, T. S.: Biochem. Pharmacol. 13, 2161 (1964)]. 1 hour after the administration of the compounds to be tested in various dosages, 100 mg./kg. of sodium barbiturate were administered intraperitoneally to the animals, and the $ED_{50}$ values of the compounds under examination were calculated from the percentage of the sleeping animals. (The control animals, receiving only sodium barbiturate in the above dosage, do not fall asleep).

The hexobarbital narcosis potentiating effect was determined by the method of Rümke et al. [Arch. Int. Pharmacodyn. 146, 10 1963)] by administering hexobarbital in a dosage of 60 mg./kg. into the tail vein of mice 1 hour after the administration of the compound under examination. The change of sleeping period was expressed in percent related to the controls.

Examination of acute toxicity

The tests were performed at room temperature (24° C.), and the death rate of the animals was observed for one week.

The pharmacological data of 1-methyl-4-carbamoyl-5-phenyl-7-chloro-1,3,4,5-tetrahydro-2H-1,4-benzodiazepine-2-one (Compound "A") determined in the above tests are listed in Table 1. For comparison, the corresponding data of the reference substances (Diazepam and Chlorodiazepoxide) are also given in the Table.

TABLE 1

| Method | $ED_{50}$mg./kg. Diazepam | p.o. (95% confidence limit) Chlorodiazepoxide | Compound "A" |
|---|---|---|---|
| Antimetrazole activity | 0.75 (0.4–1.04) | 2.47 (1.06–6.41) | 0.66 (0.26–0.93) |
| Anti-electroshock activity | 8.29 (5.97–10.98) | 23.5 (15.9–34.3) | 19.3 (13.2–25.5) |
| Antistrychnine activity | 5.71 — | 28.4 — | 26.0 — |
| Rotarod test | 3.1 (1.81–4.2) | 12.2 — | 6.7 (5.5–11.7) |
| Traction test | 4.4 (3.2–5.7) | 31.2 (7.53–52.55) | 26.9 (16.4–41.7) |
| Narcosis potentiating effect | 3.9 (1.7–6.1) | 8.1 (4.41–11.53) | 8.8 (4.0–13.2) |
| Disappearance of righting reflex | 238 (193.9–275.3) | 435.6 (327.2–511.7) | 1400 — |
| Acute toxicity ($LD_{50}$) | 815 — | 850 (691–1040) | 1678 (1516–2564) |

As appears from the data of Table II, the tetrachor spasm inhibiting effect of 1-methyl-4-carbamoyl-5-phenyl-7-chloro-1,3,4,5-tetrahydro-2H-1,4-benzodiazepine-2-one, a new compound according to the invention, is practically identical to that of Diazepam, whereas the new compound provokes muscle relaxation and sedation only in higher dosages. According to the results, the effects of the new compound are more closely related to those of Chlorodiazepoxide than of Diazepam, but with respect to the dosages provoking muscle incoordination, muscle relaxation, and narcosis potentiation in relation to the dosage provoking anticonvulsive effect, the new compound is clearly more advantageous than the reference substances. The above dosage ratios are listed in Table 2.

TABLE 2

| Compound | (1) | (2) | (3) |
|---|---|---|---|
| Diazepam | 4.3 | 7.6 | 5.2 |
| Chlorodiazepoxide | 4.9 | 11.5 | 3.3 |
| Compound "A" | 10.2 | 39.4 | 13.3 |

Notes:
(1) Rotarod $ED_{50}$: Antimetrazole $ED_{50}$
(2) Antistrychnine $ED_{50}$: Antimetrazole $ED_{50}$
(3) Narcosis potentiation $ED_{50}$: Antimetrazole $ED_{50}$ Summing up, the anticonvulsive effect of 1-methyl-4-carbamoyl-5-phenyl-7-chloro-1,3,4,5-tetrahydro-2H-1,4-benzodiazepine-2-one is identical to that of Diazepam, whereas its sedative and muscle relaxant effects are much lower, and its therapeutical index is more favorable. A single intravenous dosage of 5 mg./kg. of the new compound protects 50% of the animals against metrazole spasm even 7 hours after the administration.

The pharmacological data of some other $N^4$-substituted-1,4-benzodiazepine-2-one derivatives determined according to the above tests are listed in Table 3.

TABLE 3

| $R_1$ | $R_2$ | $R_3$ | $R_6$ | ANTIME-TRAZOLE $ED_{50}$ | ANTIELEC-TROSHOCK $ED_{50}$ i.p. | ROTAROD $ED_{50}$ | HEXOBARBITAL POTENTIATION % | $LD_{50}$ i.p. | REMARKS |
|---|---|---|---|---|---|---|---|---|---|
| Cl | $CH_3$ | $CONH_2$ | phenyl | 0.66 | 19.3 | 6.7 | 7.6 | 1678 | claimed (±) |
| Cl | $CH_3$ | $CONH_2$ | phenyl | 1.65 | 10.0 | 7.0 | 368 | 611.2 | claimed(±) |
| Cl | $CH_3$ | $CONH_2$ | phenyl | 2.2 | 8.4 | 13.0 | 112 | 661.2 | claimed(—) |
| Cl | $CH_3$ | $CONHCH_3$ | phenyl | 2.2 | 20% | 17.0 | 126 | 588.9 | derivatives |
| Cl | $CH_3$ | $CONHC_2H_5$ | phenyl | 11.5 | 40% | 14.3 | 132 | 500 | of the Japanese Patent No. 48-25199 |
| Cl | $CH_3$ | $CONHC_4H_9$ | phenyl | 20% | 20% | — | 80 | — | |
| Cl | $CH_3$ | $CONHC_6H_{11}$ | phenyl | 20% | 20% | 20% | 54 | — | |
| Cl | $CH_3$ | $CONHC_6H_5$ | phenyl | 20% | 40% | 20% | 5 | — | |
| Cl | $CH_3$ | $CONHC_8H_9$ | phenyl | 13.5 | 20% | 20% | 96 | 271.1 | derivative of our U.S. Pat. No. 4,045,483 |

The dosage in each test was 20 mg/kg of body weight of test animal and the percent values show the degree of inhibition while the nopercent values indicate the $ED_{50}$.
Note:
All dosages are expressed as mg/kg.

As appears from the data of the Table, the compound of the invention shows a very low $ED_{50}$ value (0.66 mg compound/kg body weight) in the Antimetrazole test. It means that a very low quantity of the drug can be administered to produce a tranquilizing (anxiolytic) effect in the patient. In addition the compound does not provoke muscle relaxation (see Rotarod test) and sedation (see Hexobarbital potentiation test) in this low dosage. It provokes muscle relation or sedation only in ten to twelve times higher dosages. The compounds of the invention show a selective anxiolytic effect without muscle relaxing and sedative side effects which is very important for the minor tranquillizers.

From the Table it can be seen that concerning the main effect our claimed compound shows tranquillizing (anxiolytic) effect in a 3.5 times lower dosage than the closest compound of the Japanese reference (see Antimetrazole test). Moreover our compound has a significantly lower toxicity than the closest related one of the reference (see $LD_{50}$). Qualitatively the closest related compounds shows also a selective anxiolytic effect, but quantitatively our compound is significantly more selective (see Rotarod/Antimetrazole).

Some of the compounds according to the invention exert slightly lower antimetrazole activities than Chlorodiazepoxide; it should be noted, however, that unlike Diazepam, these compounds show no or only minor sedative or muscle relaxing effects.

The effective dosage of the compounds according to the invention is generally about 2 to 20 mg, preferably 2.5 to 15 mg per day. This amount of active agent can be added either in a single dosage or in subdivided form in equal dosages. The actual dosages should always be determined on the basis of the needs of the patient and the experiences of the physician, in accordance with the type and severity of the disorders. The invention is by no means restricted to the dosage limit mentioned above.

The compounds of the formula (I), each have the same meanings as defined above, can be converted into orally, parenterally or enterally administerable pharmaceutical compositions using conventional nontoxic, inert solid or liquid carriers and/or auziliary substances. The pharmaceutical compositions may contain one or more compound(s) of the formula (I), or they may contain the compounds of the formula (I) in combination with other pharmaceutically active substances. As the carrier, e.g. water, gelatine, lactose, starch, pectine, magnesium stearate, stearic acid, talc, vegetable oils (such as peanut oil, olive oil, etc.), gum arabic, polyalkylene glycols, vaseline, etc. can be used. The active agents can be formulated to obtain solid compositions (e.g. tablets, lozenges, dragées, capsules, pills, etc.) or liquid preparations (e.g. oily or aqueous solutions, suspensions, emulsions, syrups, soft gelatine capsules, injectable aqueous or oily solutions or suspensions, etc.). The amount of the solid carrier substance may vary over wide limits; a single dosage unit contains preferably about 0.025 to 1 g of solid carrier. The compositions may contain optionally usual pharmaceutical auxiliary agents, such as preservatives, stabilizing agents, wetting agents, emulsifying agents, salts for adjusting the osmotic pressure, buffers, flavoring agents, aroma substances, etc.

The pharmaceutical compositions can be prepared by the usual pharmaceutical procedures, including e.g. screening, mixing, granulation, pressing and/or dissolution. If necessary, the compositions can be subjected to further pharmaceutical processing steps (e.g. sterilization).

The invention is elucidated in detail by the aid of the following nonlimiting Examples.

The purity grades of the produced substances were determined by thin-layer chromatography. The $R_f$ values were determined on a Stahl "C" silica-gel plate (Merck), using as eluent one of the following systems:

(1) 1:4:8 mixture of n-hexane, ethyl acetate and chloroform; (2) 1:1:8 mixture of n-hexane, acetic acid and chloroform; (3) 9:1 mixture of chloroform and methanol. The spots were developed by the chlorinetolidine technique. The melting points were determined in a dr. Tottoli-type apparatus (the melting points given in the Examples are noncorrected values). In some instances the structures of the products were identified by IR or NMR spectroscopy or by mass spectrometry.

EXAMPLE 1

1-Methyl-4-carbamoyl-5-phenyl-7-chloro-1,3,4,5-tetrahydro-2H-1,4-benzodiazepine-2-one Dry gaseous hydrochloric acid is fed for some minutes into a solution of 5.72 g (0.02 moles) of 1-methyl-5-phenyl-7-chloro-1,3,4,5-tetrahydro-2H-1,4-benzodiazepine-2-one in 20 ml of chloroform, then the separated hydrochloride is filtered off and suspended in 200 ml of acetic acid. 4.5 g of solid potassium cyanate are added to the suspension and the mixture is stirred for 2 hours at room temperature. During this time a clear solution is formed. The solution is cooled, neutralized with concentrated ammonia, the separated product is filtered off, and washed with water. 6.0 g (94.9%) of 1-methyl-4-carbamoyl-5-phenyl-7-chloro-1,3,4,5-tetrahydro-2H-1,4-benzodiazepine-2-one are obtained. The product melts at 217°–219° C. after recrystallization from ethanol. $R_f^2 = 0.28$.

Analysis: Calculated for $C_{17}H_{16}O_2N_3Cl$ (M=329.76): C: 61.95%; H: 4.9%; N: 12.7%. Found: C: 61.90%; H: 4.9%; N: 13.0%.

EXAMPLE 2

1-Methyl-4-carbamoyl-5-phenyl-7-chloro-1,3,4,5-tetrahydro-2H-1,4-benzodiazepine-2-one 0.16 g (6.85 mmoles) of metallic sodium are dissolved in 2 ml. of absolute methanol, and a suspension of 0.9 g (2.86 mmoles) of 4-carbamoyl-5-phenyl-7-chloro-1,3,4,5-tetrahydro-2H-1,4-benzodiazepine-2-one in 50 ml of absolute methanol is added to the solution at room temperature, with stirring. The suspension is stirred at room temperature for 30 minutes, and then evaporated under reduced pressure. The oily residue is dissolved in 9 ml. of dimethylformamide, and 0.48 ml of methyl iodide are added to the stirred solution at toom temperature. The mixture is stirred for an additional 2 hours, then diluted with 50 ml of water and extracted with 3×10 ml of chloroform. The chloroform extracts are combined, dried over sodium sulfate, filtered, and the filtrate is evaporated under reduced pressure, to obtain 0.85 g of a residue, which is recrystallized from ethanol. 0.75 g (79.5%) of 1-methyl-4-carbamoyl-5-phenyl-7-chloro-1,3,4,5-tetrahydro-2H-1,4-benzodiazepine-2-one are obtained; m.p.: 217°–220° C.

EXAMPLE 3

(−)-1-Methyl-4-carbamoyl-5-phenyl-7-chloro-1,3,4,5-tetrahydro-2H-1,4-benzodiazepine-2-one 2.1 g (7.32 mmoles) of (+)-1-methyl-5-phenyl-7-chloro-1,3,4,5-tetrahydro-2H-1,4-benzodiazepine-2-one are dissolved in 20 ml of benzene. 1.26 of solid sodium bicarbonate are added to the solution, and then 22 ml. of a 10% solution of phosgene in benzene are added dropwise at 10° to 15° C. The mixture is stirred for 2 hours, then 10 ml. of a 10% solution of ammonia in methanol are added, and the mixture is stirred at room temperature overnight. The separated inorganic salts are filtered off, and the filter cake is washed with benzene. The filtrate is evaporated to dryness under reduced pressure, and the residue is recrystallized from ethanol. 2.12 g. (87.5%) of (−)-1-methyl-4-carbamoyl-5-phenyl-7-chloro-1,3,4,5-tetrahydro-2H-1,4-benzodiazepine-2-one are obtained; m.p.: 214°–217° C. $[\alpha]_D^{25} = -616.5°$ (c=1, chloroform).

EXAMPLE 4

1-Methyl-4-carbamoyl-5-phenyl-7-chloro-1,3,4,5-tetrahydro-2H-1,4-benzodiazepine-2-one A suspension of 1.7 g. (4.87 mmoles) of 1-methyl-4-chlorocarbonyl-5-phenyl-7-chloro-1,3,4,5-tetrahydro-2H-1,4-benzodiazepine-2-one in 3.5 ml. of concentrated ammonia and 7 ml. of methanol is stirred at room temperature overnight. The mixture is diluted with 30 ml. of water, the separated crude product is filtered off, and recrystallized from ethanol without drying. 1.16 g. (72%) of 1-methyl-4-carbamoyl-5-phenyl-7-chloro-1,3,4,5-tetrahydro-2H-1,4-benzodiazepine-2-one are obtained; m.p.: 212°–215° C.

The following compounds are prepared from the appropriate starting substances as described in Example 4:

EXAMPLE 5

(+)-1-Methyl-4-carbamoyl-5-phenyl-7-chloro-1,3,4,5-tetrahydro-2H-1,4-benzodiazepine-2-one Starting substance: (−)-1-methyl-5-phenyl-7-chloro-1,3,4,5-tetrahydro-2H-1,4-benzodiazepine-2-one (prepared as described in Hungarian Pat. No. 160,769). Yield: 77.4%. Melting point: 215°–217° C. (after recrystallization from ethanol). $[\alpha]_D^{25} = +613.9° \pm 2°$ (c=1, in chloroform).

EXAMPLE 6

(−)-1-Methyl-4-carbamoyl-5-phenyl-7-chloro-1,3,4,5-tetrahydro-2H-1,4-benzodiazepine-2-one Starting substance: (+)-1-methyl-5-phenyl-7-chloro-1,3,4,5-tetrahydro-2H-1,4-benzodiazepine-2-one (prepared as described in Hungarian Pat. No. 160,769). Yield: 89.2%. Melting point: 215°–217° C. $[\alpha]_D^{25} = -612.8° \pm 2°$ (c=1, chloroform).

The compounds prepared according to the invention can be converted into orally administerable pharmaceutical compositions e.g. as follows:

EXAMPLE 7

4-Carbamoyl-5-phenyl-7-nitro-1,3,4,5-tetrahydro-2H-1,4-benzodiazepine-2-one

Yield: 73.5%. Melting point: 239°–241° C. (after recrystallization from ethanol). $R_f^2 = 0.22$.

Analysis: Calculated for $C_{16}H_{14}N_4O_4$ (M=326.32): C: 58.85%; H: 4.3%; N: 17.2%. Found: C: 59.1%; H: 4.5%; N: 16.8%.

EXAMPLE 8

4-Carbamoyl-5-phenyl-7-chloro-1,3,4,5-tetrahydro-2H-1,4-benzodiazepine-2-one

Yield: 98.5%. Melting point: 241°–245° C. (after recrystallization from ethanol). $R_f^2 = 0.35$.

Analysis: Calculated for $C_{16}H_{14}O_2N_3Cl$ (M=315.75): C: 60.75%; H: 4.5%; N: 15.3%. Found: C: 60.4%; H: 4.2%; N: 15.0%.

EXAMPLE 9

1-Methyl-4-chlorocarbonyl-5-phenyl-7-chloro-1,3,4,5-tetrahydro-2H-1,4-benzodiazepine-2-one Yield: 91%. Melting point: 186°–187° C. (after recrystallization from benzene). $R_f^2 = 0.8$.

EXAMPLE 10

(−)-1-Methyl-4-chlorocarbonyl-5-phenyl-7-chloro-1,3,4,5-tetrahydro-2H-1,4-benzodiazepine-2-one Starting substance: (+) 1-methyl-5-phenyl-7-chloro-1,3,4,5-tetrahydro-2H-1,4-benzodiazepine-2-one. Yield: 67.5%. Melting point: 201°–203.5° C. (after recrystallization from acetone). $[\alpha]_D^{25} = -646.5°$ (c=1, chloroform).

EXAMPLE 11

Tablets for the following composition are prepared according to the usual tabletting procedure:

| | |
|---|---|
| 1-methyl-4-carbamoyl-5-phenyl-7-chloro-1,3,4,5-tetrahydro-2H-1,4-benzodiazepine-2-one | 0.010 g |
| Lactose | 0.226 g |
| Starch | 0.125 g |
| Gelatine | 0.004 g |
| Talc | 0.012 g |
| Stearine | 0.004 g |
| Ultraamylopectine | 0.012 g |
| Colloidal silicic acid | 0.002 g. |

ADDITIONAL COMPOUNDS CONTEMPLATED BY THE INVENTION INCLUDE THE FOLLOWING (1) 1-methyl-4-carbamoyl-5-phenyl-7-bromo-1,3,4,5-tetrahydro-2H-1,4-benzodiazepine-2-one;
(2) 1-methyl-4-carbamoyl-5-phenyl-7-fluoro-1,3,4,5-tetrahydro-2H-1,4-benzodiazepine-2-one;
(3) 1-methyl-4-carbamoyl-5-phenyl-7-iodo-1,3,4,5-tetrahydro-2H-1,4-benzodiazepine-2-one;
(4) 1-methyl-4-carbamoyl-5-phenyl-7-nitro-1,3,4,5-tetrahydro-2H-1,4-benzodiazepine-2-one;
(5) 1-ethyl-4-carbamoyl-5-phenyl-7-chloro-1,3,4,5-tetrahydro-2H-1,4-benzodiazepine-2-one;
(6) 1-n-propyl-4-carbamoyl-5-phenyl-7-chloro-1,3,4,5-tetrahydro-2H-1,4-benzodiazepine-2-one;
(7) 1-isopropyl-4-carbamoyl-5-phenyl-7-chloro-1,3,4,5-tetrahydro-2H-1,4-benzodiazepine-2-one;
(8) 1-n-butyl-4-carbamoyl-5-phenyl-7-chloro-1,3,4,5-tetrahydro-2H-1,4-benzodiazepine-2-one;
(9) 1-isobutyl-4-carbamoyl-5-phenyl-7-chloro-1,3,4,5-tetrahydro-2H-1,4-benzodiazepine-2-one;
(10) 1-amyl-4-carbamoyl-5-phenyl-7-chloro-1,3,4,5-tetrahydro-2H-1,4-benzodiazepine-2-one;
(11) 1-isoamyl-4-carbamoyl-5-phenyl-7-chloro-1,3,4,5-tetrahydro-2H-1,4-benzodiazepine-2-one;
(12) 1-hexyl-4-carbamoyl-5-phenyl-7-chloro-1,3,4,5-tetrahydro-2H-1,4-benzodiazepine-2-one;
(13) 1-methyl-4-carbamoyl-5-o-chloro-phenyl-7-chloro-1,3,4,5-tetrahydro-2H-1,4-benzodiazepine-2-one;
(14) 1-methyl-4-carbamoyl-5-o-fluoro-phenyl-7-chloro-1,3,4,5-tetrahydro-2H-1,4-benzodiazepine-2-one;
(15) 1-methyl-4-carbamoyl-5-o-bromo-phenyl-7-chloro-1,3,4,5-tetrahydro-2H-1,4-benzodiazepine-2-one;
(16) 1-methyl-4-carbamoyl-5-o-iodo-phenyl-7-chloro-1,3,4,5-tetrahydro-2H-benzodiazepine-2-one, or an optically active isomer thereof;
(17) 1-n-butyl-4-carbamoyl-5-phenyl-7-nitro-1,3,4,5-tetrahydro-2H-1,4-benzodiazepine-2-one; and
(18) 1-isoamyl-4-carbamoyl-5-phenyl-7-nitro-1,3,4,5-tetrahydro-2H-1,4-benzodiazepine-2-one.

Some pharmacological data for preferred compounds (4), (17) and (18) appear in Table 4.

TABLE 4

| $R_1$ | $R_2$ | $R_3$ | $R_6$ | MELTING POINT °C. | ANTI-METRAZOLE $ED_{50}$ | ANTIELECTROSHOCK $ED_{50}$ i.p. | ROTAROD $ED_{50}$ | HEXOBARBITAL POTENTIATION % | $LD_{50}$ i.p. |
|---|---|---|---|---|---|---|---|---|---|
| $NO_2$ | $CH_3$ | $CONH_2$ | phenyl | 188–190 | 0.31 | 1.8 | 2.4 | +258 | >500 |
| $NO_2$ | $C_4H_9$ | $CONH_2$ | phenyl | 192–194 | 16.0 | 30% | 20% | +79 | >750 |
| $NO_2$ | $i-C_5H_{11}$ | $CONH_2$ | phenyl | 225–227 | 2.07 | 30% | 20% | +146 | >500 |

The footnote for Table 3 applies here as well.

We claim:

1. Racemic-1-methyl-4-carbamoyl-5-phenyl-7-chloro-1,3,4,5-tetrahydro-2H-1,4-benzodiazepine-2-one.

2. A method of tranquilizing an animal subject which comprises the step of administering to said animal subject a tranquilizingly effective amount of the compound defined in claim 1.

3. A method of treating convulsions in an animal subject which comprises the step of administering to said animal subject an anticonvulsively effective amount of the compound defined in claim 1.

4. Racemic 1-methyl-4-chlorocarbonyl-5-phenyl-7-chloro-1,3,4,5-tetrahydro-2H-1,4-benzodiazepine-2-one.

* * * * *